(12) United States Patent
Sul et al.

(10) Patent No.: US 10,646,702 B2
(45) Date of Patent: May 12, 2020

(54) MICRONEEDLE, MOULD FOR PRODUCING SAME, AND PRODUCTION METHOD FOR SAME

(71) Applicant: Paean Aesthetics Inc., Daejeon (KR)

(72) Inventors: Boojoon Sul, Daejeon (KR); Manhee Han, Daejeon (KR)

(73) Assignee: PAEAN AESTHETICS INC., Daejeon (KR)

( * ) Notice: Subject to any disclaimer, the term of this patent is extended or adjusted under 35 U.S.C. 154(b) by 601 days.

(21) Appl. No.: 14/762,275

(22) PCT Filed: Jan. 21, 2014

(86) PCT No.: PCT/KR2014/000603
§ 371 (c)(1),
(2) Date: Jul. 21, 2015

(87) PCT Pub. No.: WO2014/112854
PCT Pub. Date: Jul. 24, 2014

(65) Prior Publication Data
US 2015/0352345 A1    Dec. 10, 2015

(30) Foreign Application Priority Data

Jan. 21, 2013 (KR) .................. 10-2013-0006299
Jan. 28, 2013 (KR) .................. 10-2013-0009272

(51) Int. Cl.
*A61M 37/00* (2006.01)
*B29C 37/00* (2006.01)
(Continued)

(52) U.S. Cl.
CPC ..... *A61M 37/0015* (2013.01); *B29C 37/0092* (2013.01); *B29C 39/003* (2013.01);
(Continued)

(58) Field of Classification Search
CPC ...... A61M 37/0015; A61M 2037/0023; A61M 2037/0046; A61M 2037/0053; A61M 2037/0061; A61B 5/150984; A61B 5/685
See application file for complete search history.

(56) References Cited

U.S. PATENT DOCUMENTS 5,697,901 A * 12/1997 Eriksson .............. A61K 9/0021
514/44 R
6,290,991 B1    9/2001 Roser et al.
(Continued)

FOREIGN PATENT DOCUMENTS

JP    2008-284318 A    11/2008
KR    10-0883565 B1    2/2009
(Continued)

OTHER PUBLICATIONS

International Search Report dated May 27, 2014 in connection with PCT application PCT/KR2013/000603 (2 pages).

*Primary Examiner* — Nathan R Price
*Assistant Examiner* — Justin L Zamory
(74) *Attorney, Agent, or Firm* — Knobbe Martens Olson & Bear LLP

(57) ABSTRACT

The present invention relates to a microneedle, to a mould for producing same, and to a production method for same. More specifically, the present invention concerns a microneedle for causing a skin-beautifying substance or drug to be absorbed via the skin, to a plastic mould for producing same, and to a production method for same.

9 Claims, 3 Drawing Sheets

(51) Int. Cl.
*B29C 39/00* (2006.01)
*B29C 39/02* (2006.01)
*B29L 31/00* (2006.01)

(52) U.S. Cl.
CPC ... *B29C 39/026* (2013.01); *A61M 2037/0023* (2013.01); *A61M 2037/0053* (2013.01); *A61M 2202/0007* (2013.01); *A61M 2202/30* (2013.01); *A61M 2205/02* (2013.01); *A61M 2207/10* (2013.01); *A61M 2210/04* (2013.01); *B29K 2005/00* (2013.01); *B29K 2823/12* (2013.01); *B29L 2031/753* (2013.01); *B29L 2031/756* (2013.01)

(56) References Cited

U.S. PATENT DOCUMENTS

| | | | | |
|---|---|---|---|---|
| 2003/0045837 | A1* | 3/2003 | Delmore | A61M 37/0015 604/173 |
| 2009/0076173 | A1* | 3/2009 | Seitz, Jr. | A61K 8/26 514/770 |
| 2012/0265145 | A1* | 10/2012 | Mefti | A61M 37/0015 604/173 |
| 2014/0357544 | A1 | 12/2014 | Gonzales et al. | |

FOREIGN PATENT DOCUMENTS

| | | |
|---|---|---|
| KR | 1020100098298 A | 9/2010 |
| KR | 10-2010-0134237 A | 12/2010 |
| KR | 10-2012-0138180 A | 12/2012 |

\* cited by examiner

[Fig. 1]
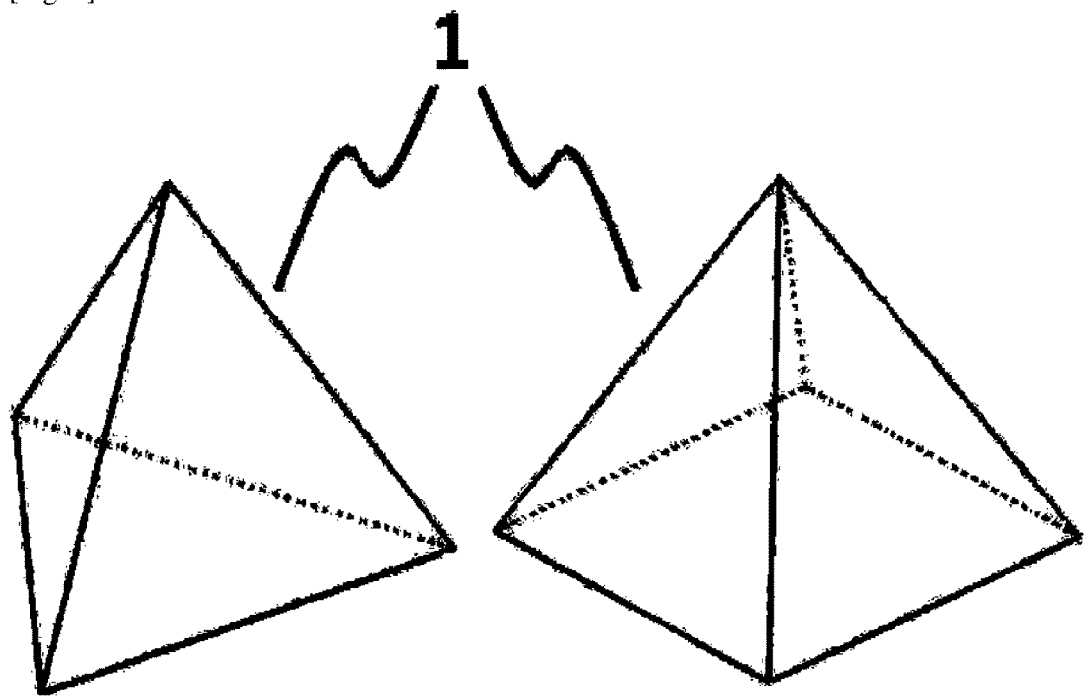
[Fig. 2]
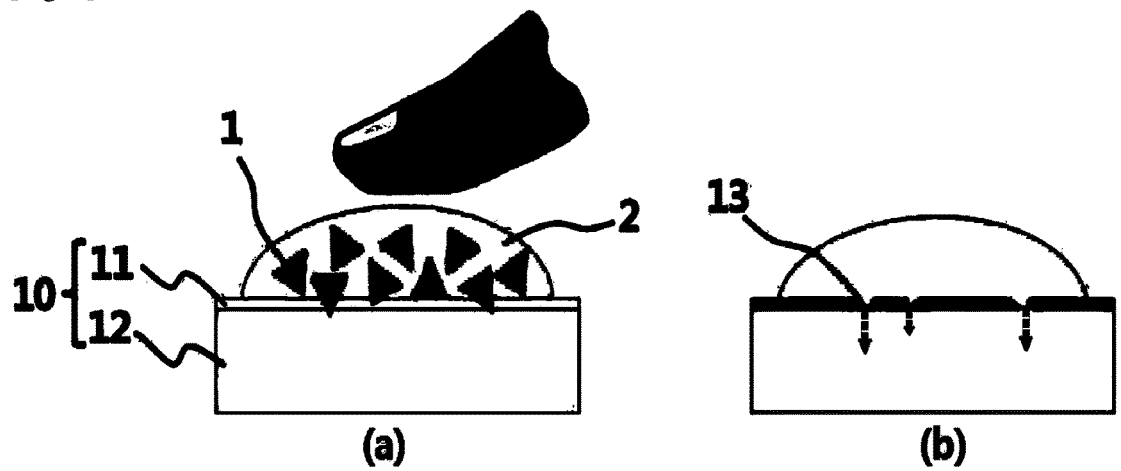
[Fig. 3]
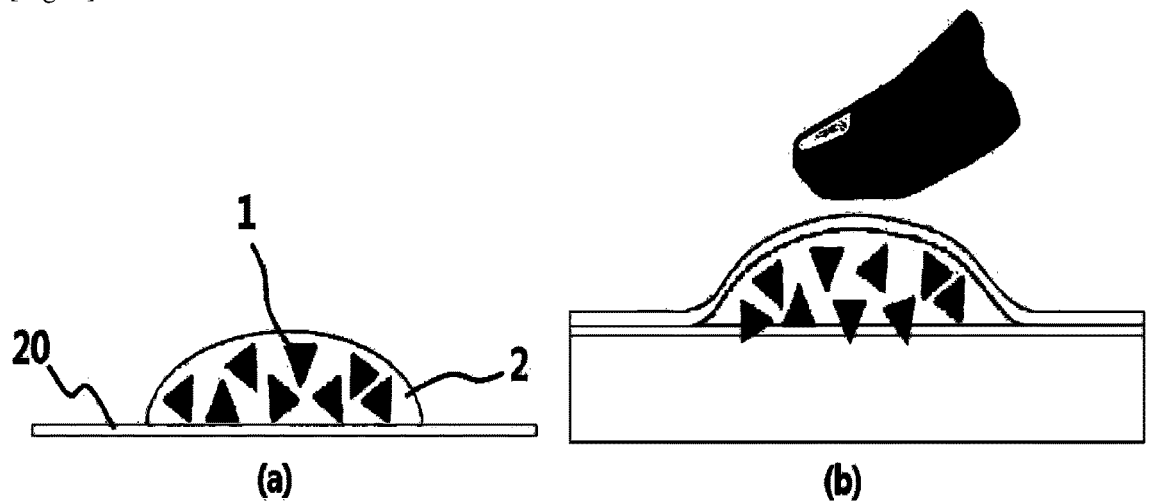

[Fig. 4]
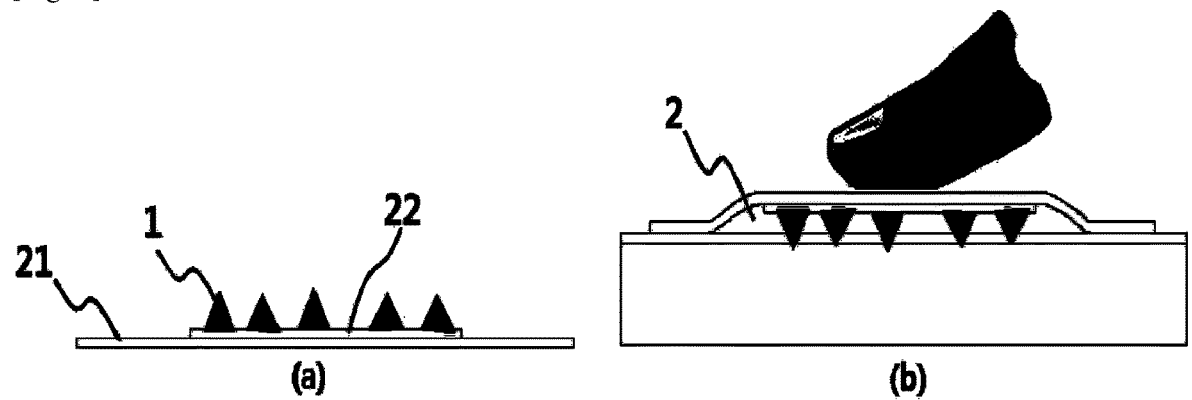
[Fig. 5]
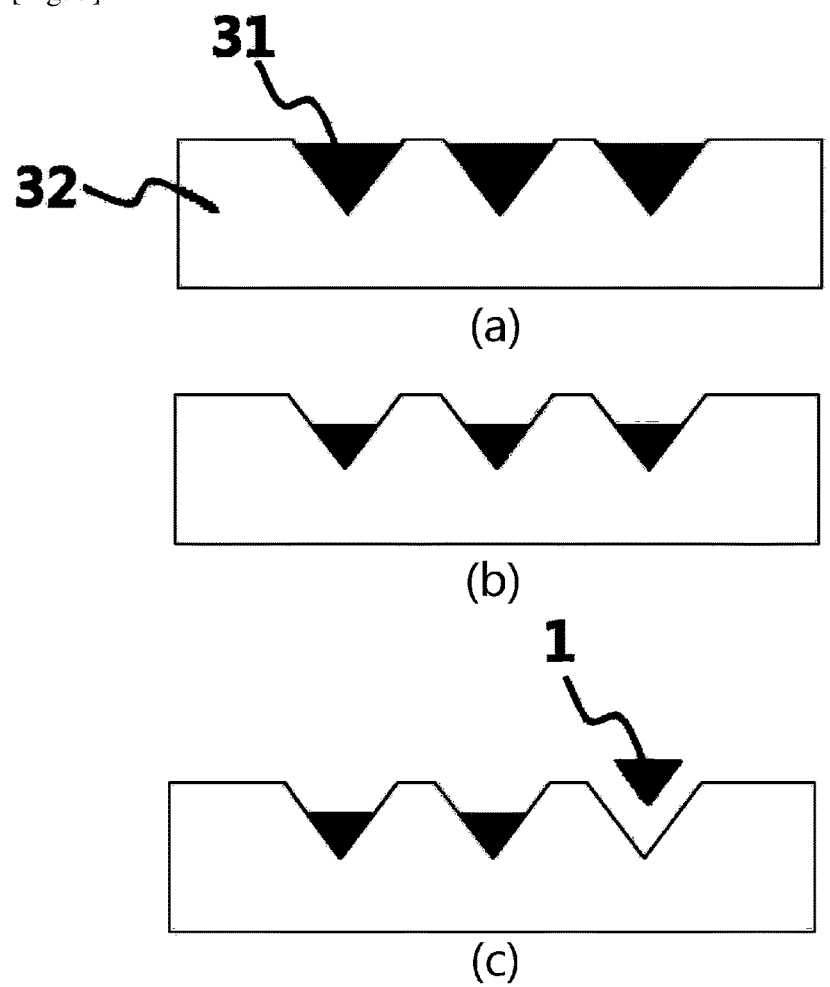

[Fig. 6]
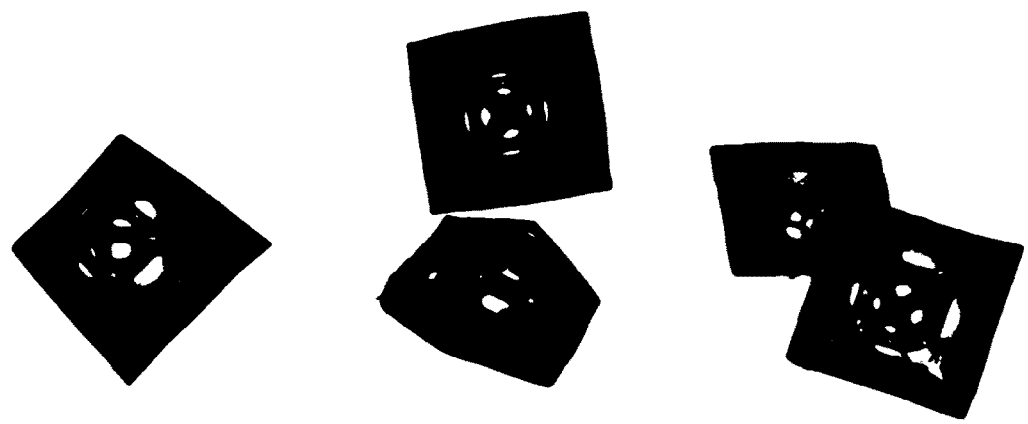
[Fig. 7]
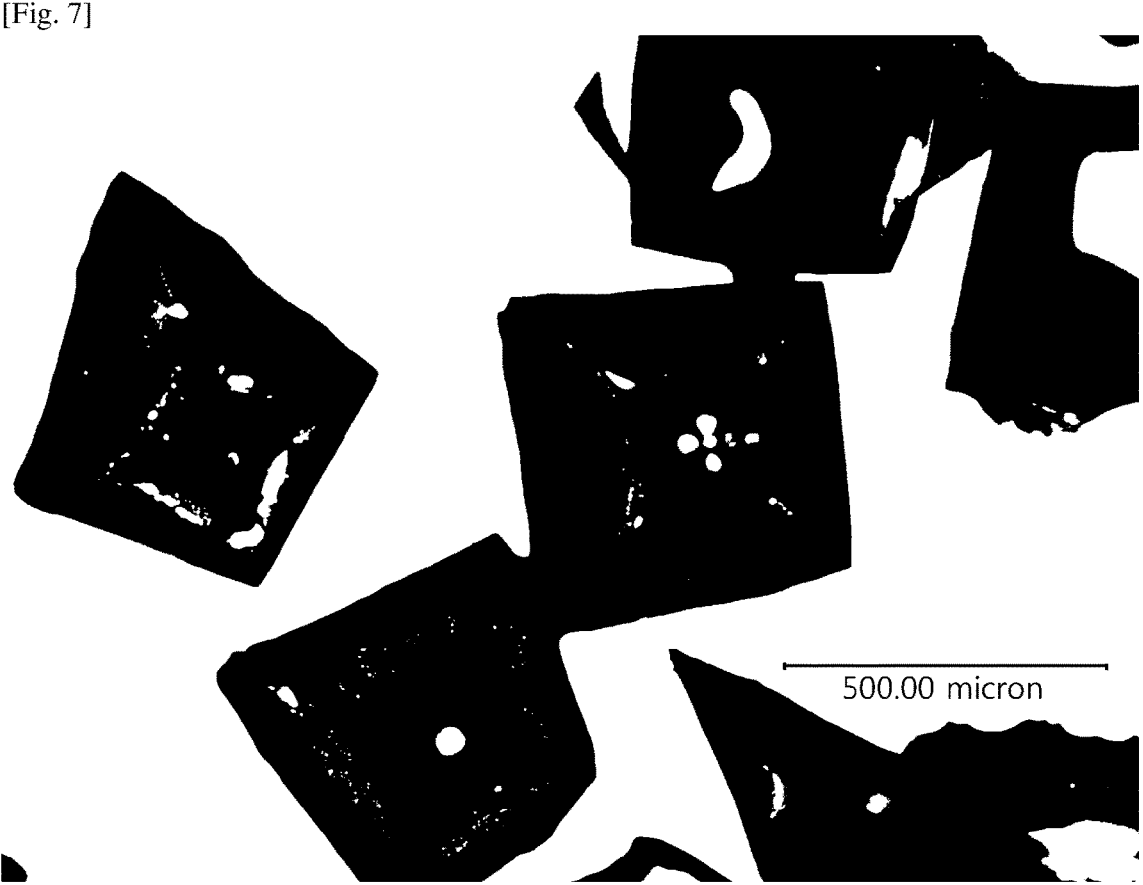

MICRONEEDLE, MOULD FOR PRODUCING SAME, AND PRODUCTION METHOD FOR SAME

TECHNICAL FIELD

The present invention relates to a micro-needle, a manufacturing mould thereof, and a method for manufacturing the same. More particularly, the present invention relates to a micro-needle for promoting the absorption of a cosmetic material or drug into the skin, a plastic mould for manufacturing the same, and a manufacturing method thereof.

BACKGROUND ART

The delivery system of useful materials such as skin care or cosmetic materials or drugs into the body by coating the skin with the materials or applying a pack or patch to the skin enjoys the advantage of allowing the continuous transport of the materials, generating no pain, and being convenient for use.

However, because the stratum corneum, which is the outermost epidermal layer of skin, is 10 μm to 60 μm thick, it serves as a barrier to the penetration of foreign matter into the body, thus a delivery system using coating or patches is very poor in absorption efficiency. Particularly, when the materials to be delivered are hydrophilic or have a large molecular weight, their absorption into the body becomes poorer.

Injection is an effective method to deliver a useful material into the body. Having dimensions of millimeters for diameter and centimeters for length, however, an injection needle stimulates many pain receptors, causing a significant pain in a subject to which the injection needle is applied. In addition, injection should be performed in hospitals or specialized skin care institutes, and cannot be easily used at home.

To overcome the drawback of conventional injection, micro-needles were developed to have a diameter of tens to hundreds μm and a length of hundreds to thousands μm. The micro-needles form micropores in the stratum corneum so that they allow materials, even though hydrophilic or large, to be readily absorbed into the skin or delivered into the body through the skin.

In addition, when applied to the site that is pierced with the conventional micro-needles, useful materials are absorbed or delivered into the body at better rates. Further, since micro-needles are too short to reach the dermis layer where nerve cells are distributed, no pain is generated upon the application of micro-needles. Even though micro-needles pierce into the dermis layer, they are smaller in diameter and length and stimulate fewer pain receptors than conventional injection needles so that the subject feels only minor pain.

WO 02/047555 discloses a device for treating the skin of a subject, including a head defining a convex head surface, and a plurality of spaced pins set in the head and protruding a predetermined distance from the head surface, and a method of treating the skin of a subject by pressing the device onto the skin of the subject with sufficient force for the pins to pierce the epidermis of the subject, leaving minute clefts in the epidermis.

U.S. Pat. No. 5,487,726 describes a percutaneous vaccine applicator system adapted to apply a vaccine to the skin and to form minute clefts in the stratum corneum.

According to WO 02/047555 and U.S. Pat. No. 5,487,726, however, it is inconvenient for the subject to use the device or the system because the dermal application of drugs and the percutaneous formation of minute clefts are conducted separately.

U.S. Pat. No. 6,603,998 discloses a method for delivery molecules into cells by coating a micro-needle-type electrode with a molecule to be delivered, and applying the electrode to the skin.

U.S. Pat. No. 6,132,755 discloses a system for the actively controlled transcorneal delivery of a medicament, in which a drug container provided with micropins is designed to allow active substance to pass through capillary openings of the micropins into the subject with the aid of a pump.

U.S. Patent Application No 2005/0251088 discloses a method for the delivery of a medicament in which the medicament stored in pores of a porous needle is percutaneously delivered when the porous needle forms minute clefts in the epidermis.

U.S. Pat. No. 3,964,482 discloses a drug delivery device, comprising a puncturing projection communicating with a drug reservoir wherein when the puncturing projection is applied to the stratum corneum of the epidermis, the drug is percutaneously administered into the skin by diffusion.

However, all of U.S. Pat. Nos. 6,603,998, 6,132,755, and 3,964,482, and U.S. Patent Application No. 2005/0251088 require additional devices for the delivery of a material of interest.

An alternative method of facilitating the transdermal delivery of a skin care cosmetic material is to use a stratum corneum-abrading cosmetic before application of the skin care cosmetic to the skin. For this, the stratum corneum may be generally removed with a scrubbing agent. The scrubbing agent must be washed off before a skin care cosmetic material is applied to the skin. Further, caution must be taken to avoid the entry of a scrubbing agent into the eye. If present in the eye, the scrubbing agent is difficult to remove. In addition to causing the sensation of foreign matter, the presence of scrubbing agent in the eye may abrade the corneum when the eye is rubbed.

Korean Patent No. 10-1206985 discloses a cosmetic composition for massaging the skin, comprising sugar scrubbers admixed with a non-aqueous cosmetic material. The cosmetic composition exhibits functions of moisturizing the skin, facilitating blood circulation, and removing dermal dead cells and corneal layers.

However, the sugar scrubbers of Korean Patent No. 10-1206985 have a general morphology of 8 or more faces, with blunt edges and large angles between the faces, and thus their scrubbing effect is not significant.

Leading to the present invention, intensive and thorough research of the present inventors into the delivery of skin care cosmetic substance or medicament resulted in the finding that tetrahedral or pyramidal micro-needles containing a dermal cosmetic material or a drug can be used as scrubbers to readily induce the percutaneous delivery of the dermal cosmetic material or the drug.

DISCLOSURE

Technical Problem

It is a primary object of the present invention to provide a micro-needle for the percutaneous delivery of skin-care cosmetic materials or drugs.

It is another object of the present invention to provide a mould, engraved with a tetrahedral or pyramidal shape, for manufacturing a micro-needle for the percutaneous delivery of skin-care cosmetic materials or drugs.

It is a further object of the present invention to provide a method for manufacturing a micro-needle for the percutaneous delivery of skin-care cosmetic materials or drugs, comprising: (i) charging an engraved mould with a solution of a skin care cosmetic material or a drug and a biocompatible material in water; (ii) dehydrating the solution to give a micro-needle; and (iii) separating the micro-needle from the engraved mould.

Technical Solution

In accordance with an aspect thereof, the present invention provides a micro-needle useful for percutaneously delivering a skin-care material or a drug.

As used herein, the term "micro-needle" refers to a tetrahedral or pyramidal micro-structure (see FIG. 1). In addition, the pyramidal micro-structure means a structure whose outer surfaces are triangular and converge to a single point at the top.

In the present invention, the micro-needle may have a planar or undulated face and/or may be empty. In addition, an edge or vertex of the micro-needle may be defected, such as partially broken.

The micro-needle may be made of a biocompatible material such as a polysaccharide, a polyvinyl alcohol, a carboxyvinyl polymer, chitosan, hyaluronic acid, a cellulose polymer, or NaCl salt. The term "biocompatible material" refers to a material that is harmless to the body and can be dissolved or degraded or can swell in water.

On one or more faces of the micro-needle, a depressed portion may be formed to a depth as long as or longer than half of the height of the micro-needle.

The micro-needle carries a skin-care cosmetic material or a drug, thus allowing the skin-care cosmetic material or drug to be effectively absorbed into the skin.

As can be seen in FIG. 2, when pressed or scrubbed against the skin after application to the skin, a micro-needle 1 including a skin-care cosmetic material 2 forms a fine cleft on the stratum corneum of the epidermis or abrades a part of the stratum corneum due to its sharp vertexes or edges.

Once crossing over the stratum corneum, which is the greatest dermal physical barrier, via the minute cleft formed in the stratum corneum or by thinning the stratum corneum, the skin care cosmetic material can easily diffused into the epidermis and dermis 12, which are both rich in water and relatively low in cell density, so that the dermal absorption of the cosmetic material can improve.

Since sharp vertexes or edges of the polygon are required to facilitate the dermal absorption, hexagons or polygons with more surfaces may not be suitable for this purpose.

In addition, if the micro-needle 1 does not dissolve, but maintains its original shape, the user must wash off the micro-needle. Further, when the micro-needle is embedded in the stratum corneum, it plugs the minute cleft, thus degrading the dermal absorption of the cosmetic material. Accordingly, the micro-needle for the percutaneous delivery of cosmetic materials or drug should preferably be either dissolved or degraded, or it should swell in water.

When the dermal cosmetic material 2 is included in the micro-needle 1, the dermal cosmetic material should not dissolve the micro-needle.

Since the epidermal stratum corneum ranges in thickness from 10 µm to 60 µm and the skin is elastic, the micro-needle preferably has a tetrahedral or pyramidal shape with a side or height ranging 50 to 500 µm in order to pierce the stratum corneum.

The dermal cosmetic material included in the micro-needle of the present invention may be an antioxidant, a growth factor, an anti-wrinkle agent, or a cell culture or culture medium.

In one exemplary embodiment, the anti-oxidant may be selected from among vitamin C and vitamin E, the growth factor from among epithelial cell growth factor (EGF) and fibroblast growth factor (FGF), and the cell culture or culture medium from among a stem cell culture and a stem cell culture medium.

A drug that may be carried by the micro-needle of the present invention may be insulin or a growth hormone.

As illustrated in FIG. 3, the tetrahedral or pyramidal micro-needle 3 may be disposed, together with the dermal cosmetic material 2, on a patch 20 applicable to the skin. When applied to the skin in this manner, the micro-needle forms a micro channel at a desired site of the stratum corneum to which the dermal cosmetic material is to be delivered, but not in the stratum corneum of the finger or palm.

In another exemplary embodiment of the present invention, as shown in FIG. 4, a plurality of the tetrahedral or pyramidal micro-needles 1 may be dispersed and arranged on a patch 21 coated with an adhesive 22 so that they are attached to the patch. When this patch is applied to the skin, the micro-needles can more effectively form micro-channels in the stratum corneum.

Not only may the tetrahedral or pyramidal micro-needle 1 be in admixture with a dermal cosmetic material 2, but also the interior of the micro-needle may be charged with a dermal cosmetic material useful for dermal rejuvenation, wrinkle removal, and skin tone improvement, or with a drug such as a vaccine, an epidermal growth factor, a growth hormone, insulin, etc.

In accordance with another aspect thereof, the present invention provides a mould, engraved with a tetrahedral or pyramidal shape, for manufacturing a micro-needle for the percutaneous delivery of a dermal cosmetic material or a drug. With reference to FIG. 5, there is a cross-sectional view of the mould according to the present invention.

The mould may be made of a plastic selected from among polypropylene, polyethylene, polyacrylate, and polycarbonate.

Also, contemplated in accordance with a further aspect of the present invention is a method for manufacturing a micro-needle for the percutaneous delivery of dermal cosmetic materials or drugs, comprising: (i) charging an engraved mould with a solution of a dermal cosmetic material or a drug and a biocompatible material in water; (ii) dehydrating the solution to give a micro-needle; and (iii) separating the micro-needle from the engraved mould.

In one exemplary embodiment of the present invention, the tetrahedral or pyramidal micro-needle 1, as shown in FIG. 5, may be manufactured by a method comprising charging an engraved mould 32 with a solution 31 containing a micro-needle constituent (biocompatible material) and water (FIG. 5a), drying the solution to give the micro-needle (FIG. 5b), and separating the micro-needle from the engraved mould (FIG. 5c).

In another exemplary embodiment of the present invention, the dermal cosmetic material may be selected from among an antioxidant, a growth factor, an anti-wrinkle agent, and a cell culture or culture medium.

In another exemplary embodiment, the anti-oxidant may be selected from among vitamin C and vitamin E, the growth factor from among epithelial cell growth factor (EGF) and fibroblast growth factor (FGF), and the cell culture or culture medium from among a stem cell culture and a stem cell culture medium.

A drug that may be carried by the micro-needle of the present invention may be insulin or a growth hormone.

The micro-needle may be made of a biocompatible material selected from among a polysaccharide, a polyvinyl alcohol, a carboxyvinyl polymer, chitosan, hyaluronic acid, a cellulose polymer, and sodium chloride.

The mould may be engraved with a tetrahedral or pyramidal shape ranging in side length or height from 50 to 500 μm.

Also, the mould may be made of a plastic selected from among polypropylene, polyethylene, polyacrylate, and polycarbonate.

Advantageous Effects

Compared to conventional techniques, the micro-needle of the present invention can allow for the dermal absorption or percutaneous delivery of a large amount of a cosmetic material or drug at higher efficiency.

In addition, the micro-needle of the present invention is structurally simple with an effective shape, and thus can be readily manufactured.

DESCRIPTION OF DRAWINGS

FIG. 1 is a perspective view of a typical micro-needle according to the present invention.

FIG. 2 is a schematic view illustrating the application of micro-needles to the body in accordance with an exemplary embodiment of the present invention.

FIG. 3 is a schematic view illustrating the application of micro-needles to the body in accordance with another exemplary embodiment of the present invention.

FIG. 4 is a schematic view illustrating the application of micro-needles to the body in accordance with a further exemplary embodiment of the present invention.

FIG. 5 is a schematic view illustrating a procedure of manufacturing micro-needles according to the present invention.

FIG. 6 is an image of micro-needles (side length=380 μm, height=300 μm) manufactured in the Example of the present invention.

FIG. 7 is an image of micro-needles (side length=700 μm, height=500 μm) manufactured in the Example of the present invention.

BEST MODE

Hereinbelow, preferred embodiments of the present invention will be described in detail with reference to the accompanying drawings. In the following description, it is to be noted that, when the functions of conventional elements and the detailed description of elements related with the present invention may make the gist of the present invention unclear, a detailed description of those elements will be omitted.

A better understanding of the present invention may be obtained through the following examples that are set forth to illustrate, but are not to be construed as limiting the present invention.

EXAMPLE

Manufacture of Micro-Structure

A silicon wafer was exposed under a patterned mask and subjected to a bulk-etching process to give a relief-engraved silicon mould. This silicon mould was plated with nickel. By a hot press, polypropylene was melted at 220° C. and pressed at a pressure of 17 kgf/cm² against the silicon mould to manufacture a plastic mould with dimensions of 9 cm×9 cm, in which about 23,400 pyramids were formed in an intaglio pattern, each having dimensions of 380 μm×500 μm and 700 μm×700 μm. A solution containing 2 g of hyaluronic acid, 4 g of water, and 200 μg of ? was loaded to depressed portions of the plastic moulds, and dried at room temperature, followed by separating the molded pyramidal micro-needles from the mould. The pyramidal micro-structures are shown in FIGS. 6 and 7.

The invention claimed is:

1. A micro-needle composition for percutaneous delivery of a dermal cosmetic material or drug, the composition comprising:
   a plurality of micro-needles; and
   a non-aqueous media comprising the dermal cosmetic material or drug,
   wherein the plurality of microneedles comprises a tetrahedral or pyramidal body with four or five pointed vertices that are not fixed to a flat base or substrate,
   wherein the plurality of micro-needles are water-dissolvable and mixed with the non-aqueous media such that the tetrahedral or pyramidal body is randomly oriented in the composition,
   wherein, when pressed against skin, any of the four or five pointed vertices of the randomly oriented the tetrahedral or pyramidal body is configured to pierce stratum corneum of the skin for facilitating the dermal cosmetic material or drug to diffuse into dermis underneath the stratum corneum.

2. The micro-needle composition of claim 1, wherein the tetrahedral or pyramidal body is made of a water-dissolvable, biocompatible material selected from the group consisting of a polysaccharide, a polyvinyl alcohol, a carboxyvinyl polymer, chitosan, hyaluronic acid, a cellulose polymer, and NaCl salt.

3. The micro-needle composition of claim 1, wherein the tetrahedral or pyramidal body has a length of 50 μm to 500 μm.

4. The micro-needle composition of claim 1, wherein the tetrahedral or pyramidal body is soluble in body fluid.

5. The micro-needle composition of claim 1, wherein the dermal cosmetic material is selected from the group consisting of an antioxidant, a growth factor, an anti-wrinkle agent, a cell culture, and a culture medium.

6. The micro-needle composition of claim 5, wherein the antioxidant is vitamin C.

7. The micro-needle composition of claim 5, wherein the growth factor is selected from the group consisting of epithelial growth factor (EGF) and fibroblast growth factor (FGF).

8. The micro-needle composition of claim 5, wherein the cell culture is a stem cell culture, and wherein the culture medium is a stem cell culture medium.

9. The micro-needle composition of claim 7, wherein the drug is selected from the group consisting of a vaccine, insulin, and a growth hormone.

* * * * *